United States Patent [19]
Sotman et al.

[11] 3,946,490
[45] Mar. 30, 1976

[54] LUBRICATION SYSTEM FOR DENTAL HANDPIECE

[75] Inventors: Kurt Sotman, Penn Wynne; Richard P. Lewis, Springfield, both of Pa.

[73] Assignee: Star Dental Manufacturing Co., Inc., West Conshohocken, Pa.

[22] Filed: Mar. 27, 1974

[21] Appl. No.: 455,456

[52] U.S. Cl. ................................ 32/28; 184/6.14
[51] Int. Cl.² .................................... A61C 1/08
[58] Field of Search ............ 32/26, 27, 28, 1, 40 R; 308/187, 84, 85, 86; 415/503; 184/95, 6.14

[56] References Cited
UNITED STATES PATENTS

| | | | |
|---|---|---|---|
| 2,090,885 | 8/1937 | Clark | 32/27 |
| 2,591,129 | 1/1943 | Brouwer | 184/1 R |
| 2,724,858 | 11/1955 | Reichert | 184/1 R X |
| 2,841,244 | 7/1958 | Sorem | 184/1 R |
| 2,841,244 | 7/1958 | Sorem | 308/187 |
| 3,052,984 | 9/1962 | Mitthauer | 415/503 |
| 3,069,775 | 12/1962 | Hawtin | 32/DIG. 1 |
| 3,195,965 | 7/1965 | Van Dorn | 308/187 |
| 3,298,103 | 1/1967 | Maurer | 32/27 |
| 3,311,429 | 3/1967 | Kocian | 308/187 |
| 3,542,442 | 11/1970 | Kent | 308/187 |
| 3,624,905 | 12/1971 | Barsby | 32/27 |
| 3,637,050 | 1/1972 | Hoffmeister | 32/27 X |
| 3,720,290 | 3/1973 | Lansky et al. | 184/6.26 |
| 3,879,851 | 4/1975 | Landgraf | 32/26 |

FOREIGN PATENTS OR APPLICATIONS 55,924   7/1922   Sweden ................................ 184/95

*Primary Examiner*—Louis G. Mancene
*Assistant Examiner*—J. Q. Lever
*Attorney, Agent, or Firm*—Caesar, Rivise, Bernstein & Cohen

[57] ABSTRACT

An air driven dental handpiece comprising a handle and a turbine housing mounted at one end thereof. The turbine housing includes a rotor having rotor blades and ball bearings for rotatably mounting the rotor. A port is formed in the handle, which is in fluid communication with the interior of the turbine housing. A lubricant is injected into the turbine housing through the port. Removable sealing means cover the port to prevent any foreign matter from entering the turbine housing and to prevent air from leaving the port.

2 Claims, 3 Drawing Figures

LUBRICATION SYSTEM FOR DENTAL HANDPIECE

This invention relates to a dental handpiece, and more particularly, to a novel air driven dental handpiece that includes a lubrication port.

Substantially all of the air driven dental handpieces now in use include a rotor that is rotatably mounted in ball bearings. The ball bearings must be periodically lubricated in order to prevent their premature wearing out. If the ball bearings wear out, they must be replaced, and the handpiece is inoperative until they are replaced.

There are presently two methods most commonly used to lubricate the ball bearings. One of these methods is to remove the end caps from the turbine housing and inject a grease lubricant into the ball bearings. This is time consuming and is a rather messy procedure. Care must be taken not to inject too much grease into the ball bearings, or it could foul the air lines in the handpiece.

The second method, which is becoming the most commonly used method, is to improve all of the external connections at the rear of the handpiece. This is accomplished by disconnecting the incoming air, water, and in some cases, light systems from the rear of the handpiece. When this is done, a lubricant can be propelled into the air line within the handpiece through the use of an aerosol can which contains the lubricant. After the lubricant has been propelled into the air line, the air, water and light systems are reconnected, and the handpiece is operated to disperse the lubricant throughout the turbine housing and out through the bearings.

Although the aerosol method of lubricating the bearings is effective to carry out the lubrication, it has been found that it suffers from a number of shortcomings. Utilizing this method, the bearings must be lubricated at least once a day. It is time consuming to disconnect all of the attachments at the rear end of the handpiece in order to carry out the lubrication. Additionally, the constantly taking apart of the handpiece will cause the rear gasket in which all of the various connections are made to wear out, and it must be periodically replaced. Of particular criticality is that the constantly taking apart of the rear end of a dental handpiece that includes an internal fiber optics system will cause wear at the interface between the incoming fiber optic system and the rear end of this system within the handpiece. This in turn diminishes the effectiveness of the light system and the continuity of the light through the sytem All of the foregoing problems are obviated by the dental handpiece of this invention. Utilizing the handpiece of this invention, an aerosol lubrication is easily accomplished without the necessity of disconnecting all of the incoming tubes into the handpiece. Furthermore, utilizing the system of this invention, a more effective lubrication is accomplished.

It is accordingly an object of this invention to provide an air driven dental handpiece having a novel lubrication system.

This and other objects of this invention are accomplished by providing a dental handpiece comprising a handle and a turbine housing mounted at one end thereof, a rotor mounted within said turbine housing, said rotor being rotatably mounted in bearings, and a port formed in said handpiece, said port being in fluid communication with the interior of said turbine housing, whereby a lubricant can be injected through said port into the interior of said turbine housing, and means for covering said port.

Other objects and many of the attendant advantages of this invention will be readily appreciated as the same becomes better understood by reference to the following description when considered in connection with the accompanying drawings wherein.

Figure 1:
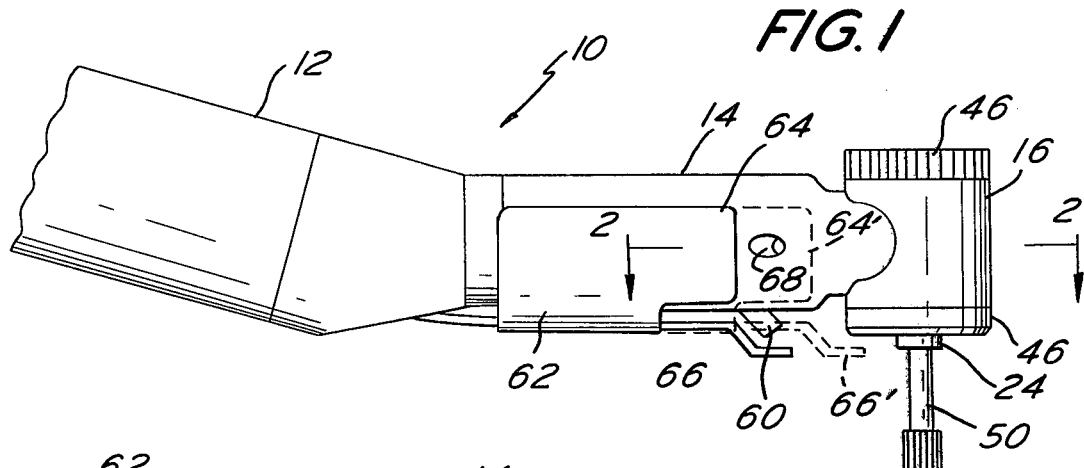
FIG. 1 is a partial side elevational view of the handpiece of this invention.

Referring now in greater detail to the various figures of the drawings wherein like reference characters refer to like parts, a dental handpiece embodying the present invention is generally shown in FIG. 1. Device 10 basically comprises a hollow handle 12 having an angled neck 14 and a turbine housing 16 secured at the end of neck 14 and projecting perpendicularly thereto.

The specific structure of the dental handpiece embodying this invention can be the same as any of the air driven dental handpieces known to the art. For example, it can comprise the structure of the handpieces shown in U.S. Pat. No. 3,120,706 or U.S. Pat. No. 3,199,196, the disclosures of which patents are incorporated by reference herein. By way of specific example, the handpiece shown in this application is the one that is disclosed in co-pending application Ser. No. 217,745, filed Jan. 14, 1972, and entitled "Air Driven Dental Handpiece", the disclosure of which application is incorporated by reference herein.

Figure 2:
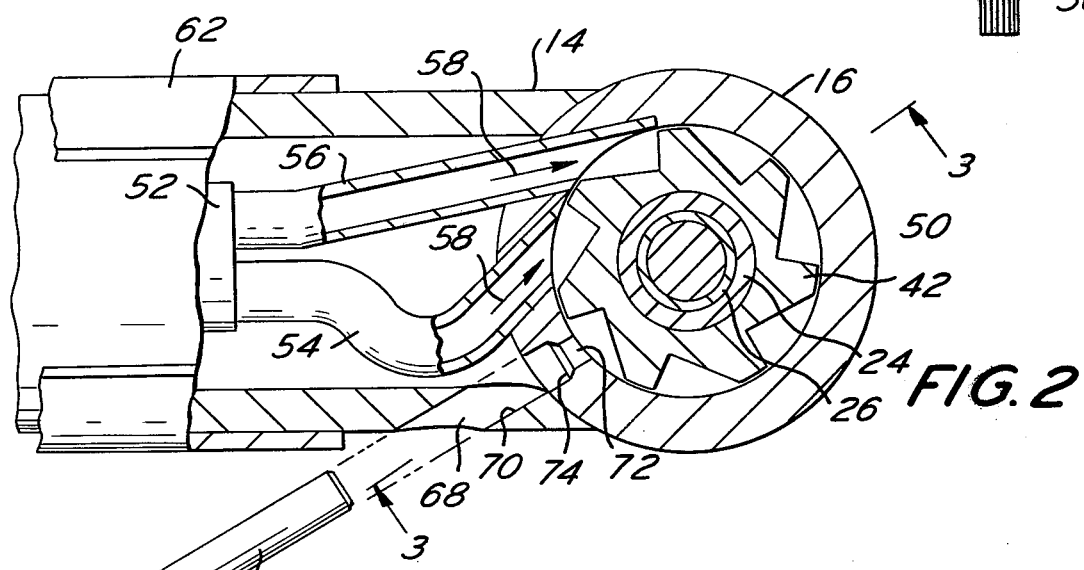
FIG. 2 is an enlarged sectional view taken along the line 2—2 of FIG. 1, and showing a lubricant tube adapted to inject a lubricant into the interior of the turbine housing.
Figure 3:
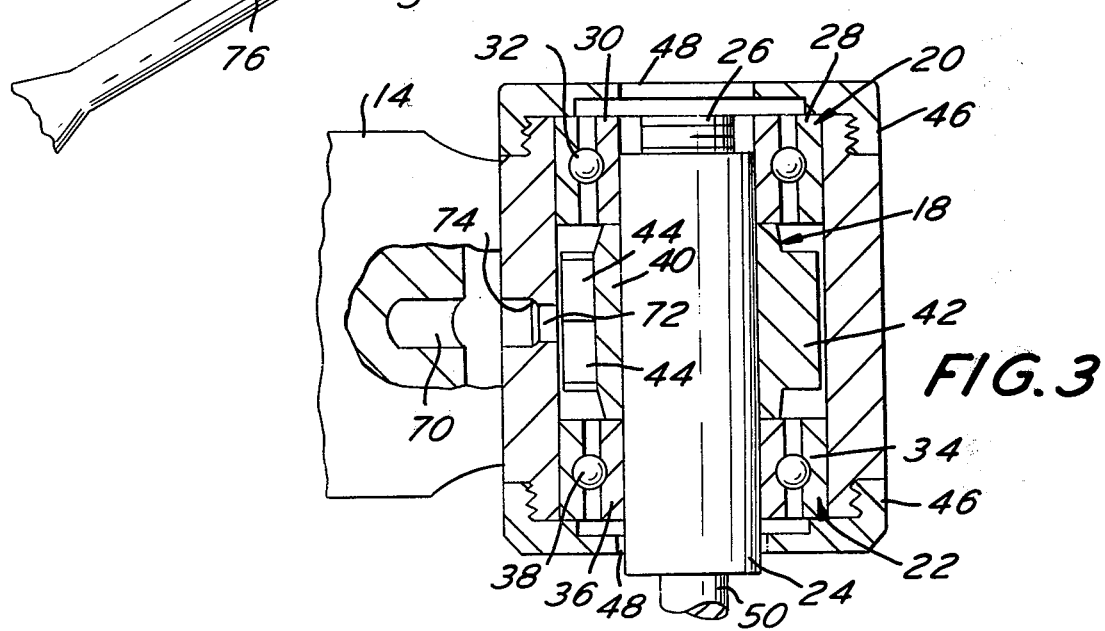
FIG. 3 is a sectional view taken along the line 3—3 of FIG. 2.

As seen in FIGS. 2 and 3, turbine housing 16 is circular in cross-section, and includes a hollow, cylindrical bore. Mounted within the bore is a turbine cartridge 18 which comprises an upper ball bearing 20, a lower ball bearing 22, a rotor shaft 24 which is internally threaded and an externally threaded collet 26. The upper ball bearing 20 includes an outer race 28, an inner race 30 and balls 32. Likewise, the lower ball bearing 22 comprises an outer race 34, an inner race 36 and balls 38. The rotor shaft 24 is secured to the inner races 30 and 36 by a pressed fit.

A rotor having a hub 40 and spaced blades 42 is secured on rotor shaft 24. To the extent described, the turbine cartridge 18 is the same as that disclosed in U.S. Pat. No. 3,120,706. In the specific embodiment of the invention shown, each blade 42 comprises a pair of aligned recesses 44. This specific structure is disclosed in aforementioned U.S. application Ser. No. 217,745. It should be understood, however, that the specific lubrication system of this invention is applicable to any air driven dental handpiece.

Turbine housing 16 is externally threaded at its top and bottom, and an end cap 46 is threadedly secured at the top and bottom of the turbine housing. The turbine cartridge 18 is insertable as a single unit into the turbine housing by removing either the top or bottom end cap, and is secured in place by the end caps. The outer races 28 and 34 are contacted by the inner surfaces of the end caps 46 which secure the turbine cartridge in place. However, each end cap is provided with an internal recess whereby the end caps will not contact the inner races 30 and 36. Accordingly, the rotor shaft is freely rotatable, along with the inner races, between the end caps. Each end cap includes a central opening 48, with the rotor shaft 24 projecting through the bottom central opening.

A dental bur 50 is secured in collet 26. The securement is made by threadedly advancing collet 26 relative to rotor shaft 24. The specific method of securement is described in greater detail in aforementioned U.S. Pat. No. 3,120,706 and U.S. application Ser. No. 217,745.

Air to rotate the turbine blades 42 is furnished by an air conduit 52 in handle 12. A pair of air tubes 54 and 56 are in fluid communication with conduit 52, and are in fluid communication with the interior of turbine housing 16. Air tubes 54 and 56 rotate the turbine by supplying air in the direction of the arrows 58 of FIG. 2.

Other details of the handpiece are the same as those disclosed in aforementioned application Ser. No. 217,745. Thus, the handpiece includes, as an optional feature, a fiber optic light tube or tubes 60 adjacent the bur 50. The handpiece also includes a water spray device for directing a coolant spray on the rotating bur 50. The water spray device includes a resilient collar 62 which is slidably mounted on section 14 of handle 12. The collar is preferably made of spring steel and resiliently grips the handle. Collar 62 includes a forward projecting portion 64.

Spray tubes 66 are secured to the underside of collar 62. The spray tubes 66 are adapted to supply a coolant spray to the rotating bur 50 when the handpiece is in use. The spray tubes 66 are movable to the position shown in phantom at 66' in FIG. 1 when they are in use for directing the coolant to the bur. They are movable rearwardly, by sliding collar 62, to the position shown in full line when the end caps 46 are removed in order to obtain access to the turbine cartridge 18 and in order to permit the lubrication of the handpiece, as will be explained hereinafter. The rigid spray tubes 66, which are formed from stainless steel, are connected within handle 12 to flexible tubing. Further details on the spray tubes and their internal connections can be found in aforementioned U.S. Pat. No. 3,199,196 or aforementioned application Ser. No. 217,745. By way of example, the spray device 66 can comprise a pair of adjacent tubes, with one being for water and the other for air, or a single spray device which can dispense a mixture of air and water, or water or air alone.

Section 14 of handle 12 includes an opening 68 formed therein. Opening 68 leads to a channel 70 (FIG. 2) which in turn is connected to channel 72. Channel 72 is of a smaller diameter than channel 70. A shoulder 74 is formed at the base of channel 70 and adjacent channel 72.

The handpiece is lubricated by sliding the collar 62 to the position shown in full line in FIG. 1. Thereafter, tube 76 is inserted in channel 70 through opening 68 until the forward tip of the tubes rests on shoulder 74. The tube 76 is in turn connected to the discharge port of an aerosol can containing a lubricating and/or cleaning fluid. The valve on the aerosol can is depressed, and the entrained lubricant is injected into the interior of the turbine housing 16 through channel 72. Thereafter, tube 76 is removed and the spray clip 62 is pushed forwardly until the projecting portion 64 covers opening 68, and is in the position shown in phantom at 64' in FIG. 1.

With the opening 68 thus covered, the handpiece is actuated by admitting air into the air supply conduit 52. This causes the rotor blades 42 to rotate and disperse the lubricant. Most of the lubricant will be entrained in the exhaust air, and leave through the exhaust channel within the handpiece. However, a portion of the exhaust air passes through the ball bearings 20 and 22 by passing between the inner and outer races. This portion of the exhaust air then passes through the openings 48 in the end caps 46. In this way, the balls and the associated raceways of the bearings are lubricated. Any of the lubricating fluids known to the art can be used in carrying out this invention. By way of example, the aerosol can can contain a mixture of mineral oil, which serves as a lubricant, a Freon solvent and a propellent, such as Freon 12. The solvent acts as a cleaner for the ball bearings.

The cleaning and lubricating method can be carried out on a periodic basis, and normally if it is done at the close of each day, this is sufficient to keep the ball bearings well lubricated. The shoulder 74 serves as a stop for the insertion of the tube 76, and insures that the tube will not inadvertently be projected all the way into the turbine housing, where it will encounter interference from the turbine blades. By the same token, the shoulder 74 insures that the tube will be inserted sufficiently far to obtain proper dispersion of the lubricant within the turbine housing.

The projecting portion 64 on the clip 62 thus serves a dual function. One function is to seal the opening 68 in order to insure proper dispersion of the lubricant when the handpiece is being lubricated. The second function is to keep the opening 68 closed during the use and storage of the handpiece. Thus, when the handpiece is being used, no exhaust air will leave through the opening 68, but instead, the bulk of the exhaust air will leave through the exhaust conduit within the handle 12 (See aforementioned application Ser. No. 217,745). Additionally, no dirt or other contaminant can enter the handpiece through opening 68 when the handpiece is being stored.

It is accordingly seen that the handpiece can conveniently and easily be lubricated without the necessity of removing the end caps and without the necessity of disassembling the handpiece from the connecting tubes at the rear. The lubricant is injected directly into the turbine housing, and this insures complete lubrication.

It should be understood that other means of sealing the opening 68 can be provided. Thus, there can be a pivoted cover on the handle of the handpiece. However, the clip 62 is preferred since it is easily moved into and out of position, and additionally serves the added function of supporting the spray tube or tubes 66. The lubrication system of this invention is adapted for use with any handpiece having unshielded bearings. Thus, when the air turbine is rotated, a portion of the exhaust air will pass through the unshielded raceways of the bearings, thereby lubricating the bearings.

In the embodiment of the invention shown, the opening 68 is in handle 12, and the channel projects angularly into the turbine housing 16. This position is preferred because the opening 68 is readily coverable by the collar 62. Since collar 62 is already on the handpiece, it is a relatively simple matter to extend the collar to include the projection 64, and therefore no ancillary cover means is needed for opening 68. However, the invention can also be carried out by having the opening and channel directly formed in turbine housing 16. When this is done, a separate cover will have to be provided. Accordingly, the only critical feature is that the channel for conveying the lubricant open into the turbine housing in the area between the bearings so that the upper and lower bearings are both lubricated when air is admitted to rotate the rotor.

Without further elaboration, the foregoing will so fully illustrate my invention, that other may, by applying current or future knowledge, readily adapt the same for use under various conditions of service.

What is claimed as the invention is:

1. A dental handpiece comprising a handle and a turbine housing mounted on one end thereof, a rotor mounted within said turbine housing, said rotor being rotatably mounted in bearings, said bearings comprising upper and lower bearings, with said rotor being mounted between said upper and lower bearings, a port formed in said handle, said port being in fluid communication with the interior of said turbine housing, said port comprising a channel formed in said handpiece, said channel having an opening in said turbine housing, said opening being positioned between said upper and lower bearings, and a collar secured on said handle and slidable relative thereto, said collar being adapted to cover said port, whereby a lubricant can be injected through said port into the interior of said turbine housing.

2. A dental handpiece comprising a handle and a turbine housing mounted on one end thereof, a rotor mounted within said turbine housing, said rotor being rotatably mounted in ball bearings, said turbine housing having upper and lower openings, a port in said handle, said port being in fluid communication with the interior of said turbine housing, and a collar secured on said handle and slidable relative thereto, said collar being adapted to cover said port, whereby a lubricant can be injected through said port into the interior of said turbine housing, and whereby said injected lubricant is propelled through said ball bearings and through said openings when said rotor is air actuated.

* * * * *